United States Patent
Weller

(10) Patent No.: US 7,280,189 B2
(45) Date of Patent: Oct. 9, 2007

(54) METHOD AND APPARATUS FOR TESTING OPTICAL FIBER BASED NETWORKS

(76) Inventor: Whitney T. Weller, 4 Tamarind La., Exeter, NH (US) 03833

( * ) Notice: Subject to any disclaimer, the term of this patent is extended or adjusted under 35 U.S.C. 154(b) by 0 days.

(21) Appl. No.: 11/301,688

(22) Filed: Dec. 13, 2005

(65) Prior Publication Data

US 2006/0092404 A1    May 4, 2006

Related U.S. Application Data

(63) Continuation-in-part of application No. 10/710,410, filed on Jul. 8, 2004, now abandoned.

(51) Int. Cl.
*G01N 21/00* (2006.01)
(52) U.S. Cl. .................................... 356/73.1
(58) Field of Classification Search ............. None
See application file for complete search history.

(56) References Cited

U.S. PATENT DOCUMENTS

| | | | | |
|---|---|---|---|---|
| 4,883,054 A | * | 11/1989 | Fuller et al. | 606/12 |
| 5,187,362 A | | 2/1993 | Keeble | |
| 5,311,344 A | | 5/1994 | Bohn | |
| 5,396,569 A | * | 3/1995 | Yanagawa et al. | 385/24 |
| 5,859,936 A | | 1/1999 | Ishikawa | |
| 6,028,661 A | * | 2/2000 | Minami et al. | 356/73.1 |
| 6,396,575 B1 | | 5/2002 | Holland | |

OTHER PUBLICATIONS

Measuring the Individual Attenuation Distribution of Passive Branched Optical Networks, Tanaka, Tateda, Inoue, IEEE Photonics Technology Letters, vol. 8, No. 7, Jul. 1996, p. 915-917.
Original method for analyzing multipaths networks by OTDR measurement, J. Laferriere, M. Saget, A. I hampavere, OFC 97, p. 99-101, 1997.
A New Fault-Identification Method Using a Dichroic Reflective Optical Filter in Optical Subscriber Loops, Takasugi, Tomita, Suzuki, and Akai, Journal of Lightwave Technology, vol. 11, No. 2, Feb. 1993 p. 351-357.
New Method of In-Service Fault Localisation in Passive Optical Subscriber Loops, J. W. Verhoof, Electronics Letters May 21, 1992 vol. 28 No. 11, p. 1059-1061.

* cited by examiner

*Primary Examiner*—Tu T. Nguyen
(74) *Attorney, Agent, or Firm*—Shalom Wertsberger; Saltamar Innovations

(57) ABSTRACT

A method offering the capacity for safe in service testing of optical network using time domain reflectometer is disclosed. The network utilizes end equipment devices having filters designed to reject specific frequency range, and preferably a frequency range that lies between two desired frequency ranges. The signal used for the reflectometer is specifically selected to be within the rejected frequency range. The selection of the reflectometer frequency allows for in use testing without effecting the desired frequencies, as well as minimizing damage to sensitive components within the end equipment devices.

18 Claims, 7 Drawing Sheets

METHOD AND APPARATUS FOR TESTING OPTICAL FIBER BASED NETWORKS

RELATED APPLICATIONS AND MATERIAL

The present application is a continuation in parts of U.S. application Ser. No. 10/710,410 filed on Jul. 8, 2004 now abandoned to the present inventor which is incorporated herein by reference. This application also explicitly references disclosure document No. 550769 received in the USPTO Apr. 6, 2004, which is also incorporated herein by reference.

FILED OF THE INVENTION

The present invention relates to testing of optical fiber networks such as passive optical networks (PON) and Fiber to the Premises (FTTP) networks, and more particularly to a method and an apparatus for performing such testing without cessation of service during testing.

BACKGROUND OF THE INVENTION

While the following specifications relate to any optical fiber distribution center, the specifications will utilize the common construction of a passive optical network (PON and Fiber to the Premises networks. However the skilled in the art will readily recognize the applicability of the invention to other optical fiber networks, and the invention extends thereto.

In their most common embodiments, passive optical networks comprise of a fiber connecting a wire center 100 to a branching device (commonly known as a splitter or a splitter coupler 6. These specifications will use the term splitter to encompass all such branching and or branching/coupling devices), and from the splitter 6 to a plurality of other downstream network devices. A simplified example of such network is depicted in FIG. 1, and generally follows ITU (International Telecommunication Union) G.983 standard. A wire center 100 is any point of distribution, such as a service provider voice and data signal collection center, a repeater site, and the like. The wire center is the service provider distribution end, and contains at least one Optical Line Terminal (OLT) 1 which serves to couple data to fibers, that in a typical installation extend for a distance of between 20-40 Km between the wire center and the splitter and thence the user premise location. A trunk fiber 4 connects to a splitter or a splitter/coupler 6, which divides the incoming data stream into a plurality of downstream optical devices such as an Optical Network Terminal (ONT) 5 which are commonly installed in a user premises. Feeder fibers 7 connect the ONT to the splitter. The user premises, splitter, and the wire center are considered remote to each other, however no specific distance is dictated.

A common method for diagnosing and testing optical networks utilizes Optical Time Domain Reflectometry. The reflectometer sends an optical pulse into the network, and analyses returns from the network. Every network is characterized by a 'signature' of distribution branch returns. Problems in the network may be analyzed by the nature of the reflections. An example of an optical time domain reflectometer employed for such purposes can be found in U.S. Pat. No. 6,028,661 to Minami et al.

However use of Reflectometry suffers from several shortcomings, two of which are service disruption and a potential for equipment damage. Present Reflectometry techniques call for using a band in which the attenuation is minimized. However this band is also the band which is used for the transmission of data. U.S. Pat. No. 6,396,575 to Holland also calls for use of out of band frequency range, but discloses a band of 1625-1650 nM, to avoid the 1550 nm band. As can be seen in FIG. 3, ITU G.983 calls for PON using a high band of 1550 nM 10b, and two low band ranges of 1490 12b and 1310 nM 9b respectively. The skilled in the art will recognize that those frequencies are used by way of example, and because they are conformant to the ITU G.983 standard, however the invention is applicable to other ranges as well. Data carrying frequencies, either to or from the data center are commonly referred to as payload frequencies.

End equipment such as OLT's use an optical filter 15 to separate the signal to distinct bands. FIG. 3 depict the schematic characteristic of such filters. After being separated by the filter each band is direct to a detector such as a PIN diode based detector (9b, 10b). Such detectors are limited by their signal handling capacities and may be damaged by excessive signal levels.

Testing of a typical PON requires use of high level signals due to a typical high attenuation in areas such as the splitter and the fiber feeders themselves, in addition to the downstream attenuation of the trunk fiber 4. The test signal needs to travel, and thus be attenuated, in both directions, and still be detected in usable levels for analysis. Such high signal levels can oftentimes damage the detectors at the user premises. Thus, utilization of the test band of 1625-1650 nM as proposed for example by Holland may cause damage to the end equipment.

Regular in-service testing of the network offers advantages to network operators by providing the ability to allow single dispatch for cost effective speedy repair breakdowns, and by being able to identify and address problems before they become critical. Therefore there is a clear and as of yet unresolved need for a system that will offer such solution.

SUMMARY OF THE INVENTION

One aspect of the invention solves the problem of in-service testing of optical networks by providing in service time domain Reflectometry which operates at or about the frequency area that is rejected by the end-equipment filters, which when used in a ITU G.983 network is the frequency zone between the payload frequencies of the high band range of 1550 nM, and the two low band ranges of 1490 and 1310 nM.

Therefore there is provided a system for testing optical networks in an optical network having a trunk fiber optic having a proximal and a distal ends, the trunk being coupled at its proximal end to an Optical Line Terminal (OLT) and its distal end coupled to a splitter, the splitter being further coupled to a plurality of feeder optical fibers, each coupled to an Optical Network Terminal (ONT), the ONT having an optical passband filter having at least one optical frequency rejection zone for attenuating signals in frequencies of the rejection zone, the system comprising an Optical Time Domain Reflectometer (OTDR) coupled to the trunk at or near its proximal end, wherein the OTDR having a transmitter tuned to produce optical waves in a primary frequency within the rejection zone, for the OTDR to couple transmitted waves to the trunk, and a receiver tuned to receive reflected optical waves at a frequency within the rejection area, for receiving the transmitted optical waves reflected from the optical network. The data set of reflected waves at the OTDR frequency forms a network signature. The splitter and other network components may be passive or active components.

Preferably the optical filter also has a high passband and a low passband, wherein the rejection zone is interposed between the high and low passbands.

It is noted that each network will have at any given state a 'reflection signature', i.e. data associated with a typical set of returned reflected waves. Changes to the network—whether as a result of changing the network configuration, or as a result of problems or breakdowns, will be reflected in the signature. Therefore an analysis of differences between the signature of a network in good condition and a signature of the same network that differs from such known-good network may be utilized to analyze network problems and possibly to warn against network deterioration that calls for preventive repairs.

In preferred embodiments, the system further comprises a computer 500 and a computer program (implemented in hardware, software, a special purpose circuitry, or a combination thereof) capable of analyzing the reflected optical waves. Preferably the system further comprises a storage module to store at least one reflection signature. In the more preferred embodiment, the program comprises a comparator for comparing a first reflection signature and a second reflection signature. In the most preferred embodiment, the program further comprises an analyzer for analyzing the difference from the comparison module, and an alerter for alerting network personal of analysis results that diverge from certain guidelines, indicating a possible network problem. As stated above, each of those components may be implemented in hardware or software.

Preferably, the transmitter and receiver are integrated within the OTDR. More preferably, the OTDR is further constructed to measure the reflected optical waves. In the preferred embodiment, the OTDR is constructed to provide the computer with data relating to time delay between the transmission of a transmitted optical wave and reception of corresponding reflected waves. In the most preferred embodiment, the OTDR is constructed to provide the computer with data relating to the amplitude of the reflected optical wave, or with an attenuation level of the reflected wave.

In another aspect of the present invention there is provided a method for testing optical networks in an optical network having a trunk fiber optic having a proximal and a distal ends, the trunk being coupled at its proximal end to an Optical Line Terminal (OLT) and its distal end coupled to a splitter, the splitter being further coupled to a plurality of feeder optical fibers, each coupled to an Optical Network Terminal (ONT), the ONT having an optical passband filter having a at least one optical frequency rejection zone for attenuating signals in frequencies of the optical filter rejection zone, the method comprises the steps of coupling optical waves having a frequency within the rejection area to the proximal end of the trunk, receiving the transmitted optical waves reflected from the optical network, and measuring characteristics of the reflected waves. Preferably the method further comprises the step of analyzing the characteristics. Also preferably, the method further comprises the step of storing a characteristic reflection signature of the network, i.e. a data set representing data about the reflected waves. More preferably, the method further comprises the step of comparing at least a stored signature and a second signature, such as a current signature or another stored signature, to derive differences therebetween.

Most preferably the method comprises the step of alerting users of differences between the stored and second signature, when the differences correspond to selected criteria.

The apparatus and the method of the different embodiments may extend to a plurality of trunk line/feeder line combinations by allowing switching of the OTDR signals between a plurality of trunk fibers.

SHORT DESCRIPTION OF DRAWINGS

The summary above, and the following detailed description will be better understood in view of the enclosed drawings which depict details of preferred embodiments. It should however be noted that the invention is not limited to the precise arrangement shown in the drawings and that the drawings are provided merely as examples.

DETAILED DESCRIPTION

Figure 1:
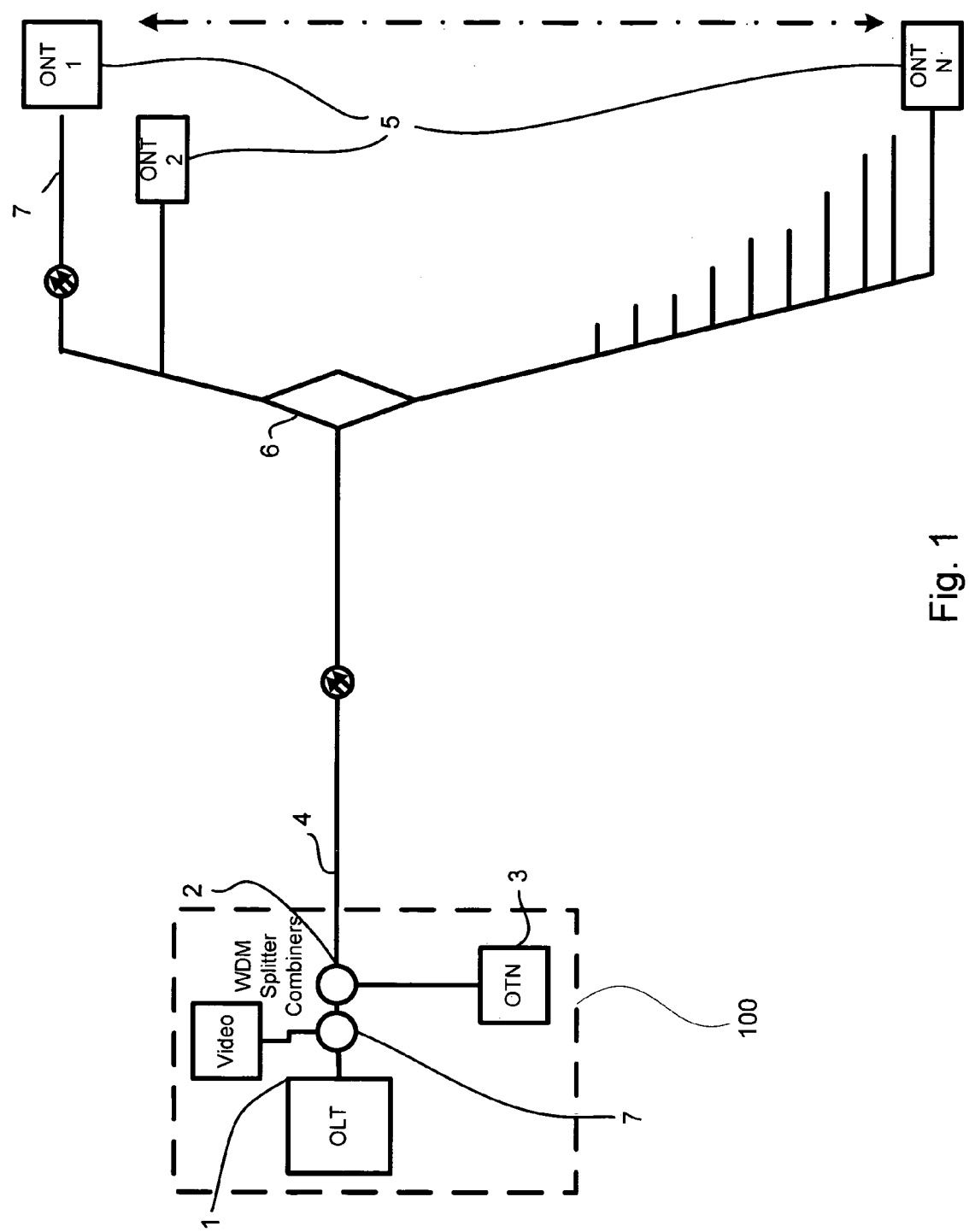
FIG. 1 depicts a schematic view of a typical ITU G.983 Optical Networks.

The first aspect of the present invention calls for testing of the network without disruption for service and while preventing damage to the network equipment, more particularly optical edge equipment, due to high energy test pulses. FIG. 1 depicts a simplified diagram of such embodiment. In a wire center 100 an Optical Line Terminal (OLT) 1 is provided. The OLT directly or indirectly couples signals such as video, data, voice and the like, into a trunk fiber 4, and receives information therefrom. Oftentimes, other devices, such as video sources 6 also couple directly or indirectly, analog or digital signals into trunk fiber 4 at the wire center, most commonly by way of a multiplexer 7. The trunk fiber has a proximal end at the wire center, and a distal, or remote, end coupled to a splitter 6. It should be noted that the other devices or parts such as connectors, splices, and the like, may be interposed between the wire center and splitter, but the principle is that a signal sent down the proximal end will arrive at the splitter, and trunk fiber 4 should be considered as extending to such devices or parts if they are used. Attenuation of that signal will depend on the characteristics of the network, and the propagation delay along the fiber will depend primarily on the distance and fiber characteristics such as propagation factor, and the like. The splitter divides the signal into a plurality of branches. A plurality of feeder fibers 7 extend from the splitter to the user premises. At the user premises the feeder fiber is coupled to an Optical Network Terminal (ONT) 5. It should be noted that typically the wire center will have a plurality of trunk fibers, coupled to one or more OLT or multiplexers, with more signal generators like the OLT 1 and video source 6, coupled to the plurality of trunk lines.

The preferred embodiment couples an Optical Test Node 3 to the proximal end of the trunk fiber 4 via a combiner 2. The combiner may comprise any device capable of coupling a signal to the network and receiving signals of a predetermined band therefrom, while allowing other signals to flow therethrough.

Figure 2:
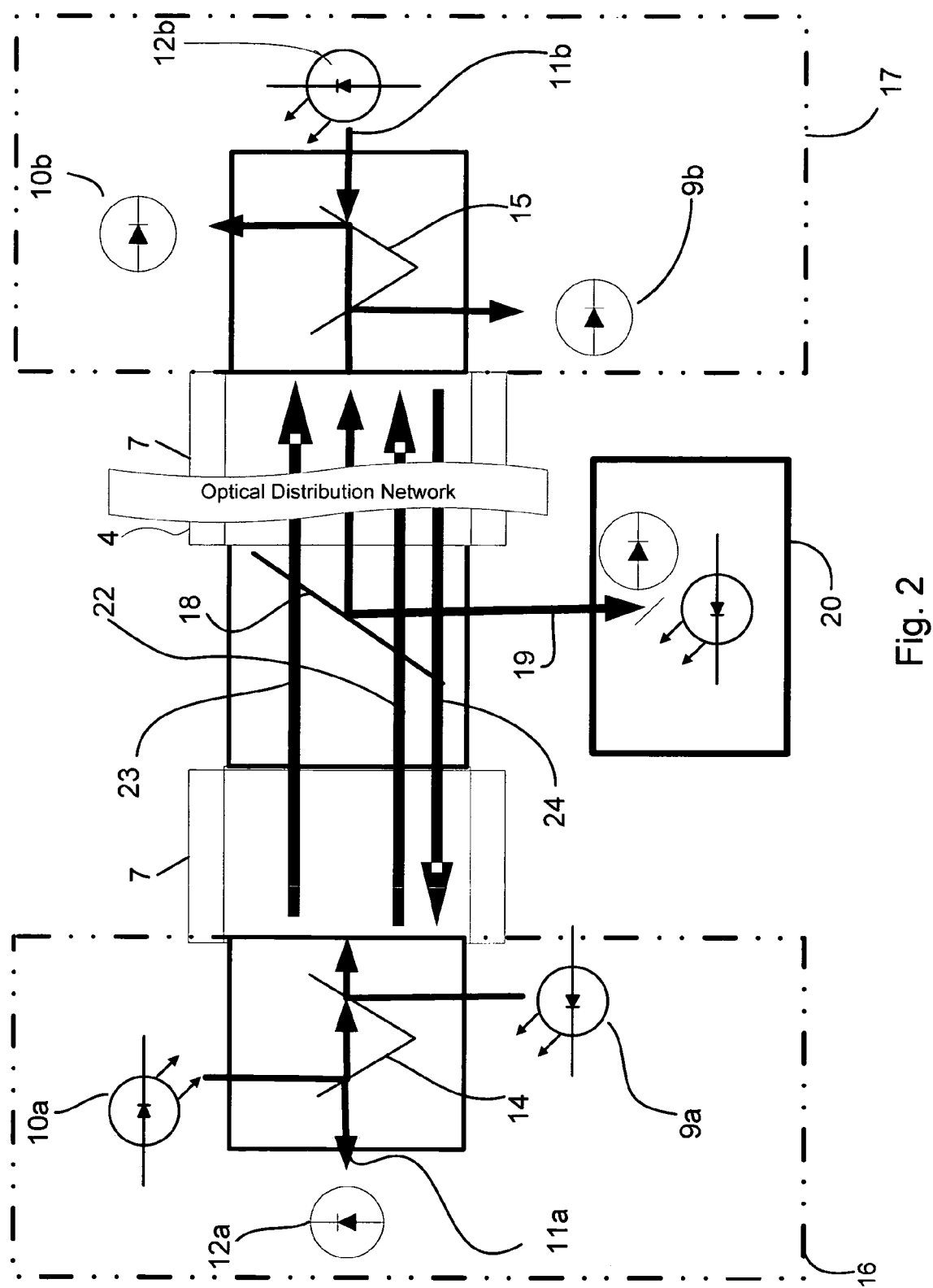
FIG. 2 depicts a simplified expanded view of signal flow in certain components of various components of an optical network.

FIG. 2 depicts a simplified diagram of signal flow in some key components of the preferred embodiment. The OLT transceiver 16 is shown having an optical filter/signal splitter/combiner 1 (commonly, and hereinafter referred to as triplexer) which utilize various combinations of optical filters and/or mirrors to feed a signal from several sources 9a, 10a, to the fiber for downstream transmission, and transfer signals 11(a) received from the from the fiber ("upstream transmission") to photodetectors such as 12a.

Combiner 2 is also coupled to the proximal end of the trunk fiber 4 and preferably interposed between the sources and the proximal end, closest to the proximal end from all other signal sources in the wire center. Combiner 2 is constructed to pass signal frequency bands like 22,23, and 24 with minimal interference. It is further constructed to accept a signal 19 of specific frequency band (referred to as OTDR signal hereinafter) from an OTDR optical interface 20. Combiner 2 couples the OTDR signal into the trunk fiber, and returns reflections of the OTDR signal to OTDR interface 20. The skilled in the art will readily recognize that the functions of coupling the OTDR signal to the trunk fiber, and of receiving the OTDR reflections from the trunk fiber and sending it to the OTDR may preferably be performed by a single combiner, or may be performed by separate devices, and that the OTDR may comprise a single unit for sending and receiving signals or may comprise a plurality of distinct units. By way of example, combiner 2 may utilize a frequency selective mirror 18, as known, to achieve the directing of the OTDR signal 19 to and from the OTDR.

The various signals coupled to trunk fiber 4 are split by splitter 6 into a plurality of feeder fibers 7. FIG. 2 also depicts the signal flow in an Optical Network Terminal (ONT) coupled to such feeder fiber 7. In somewhat similar fashion to the arrangement of the OLT transceiver 16, the ONT transceiver 17 is equipped with triplexer 15 which splits the signal according to frequency bands that are coupled to photodetectors 9b and 10b, and signal source 12b which sends signal 11b upstream to the wire center.

Figure 3:
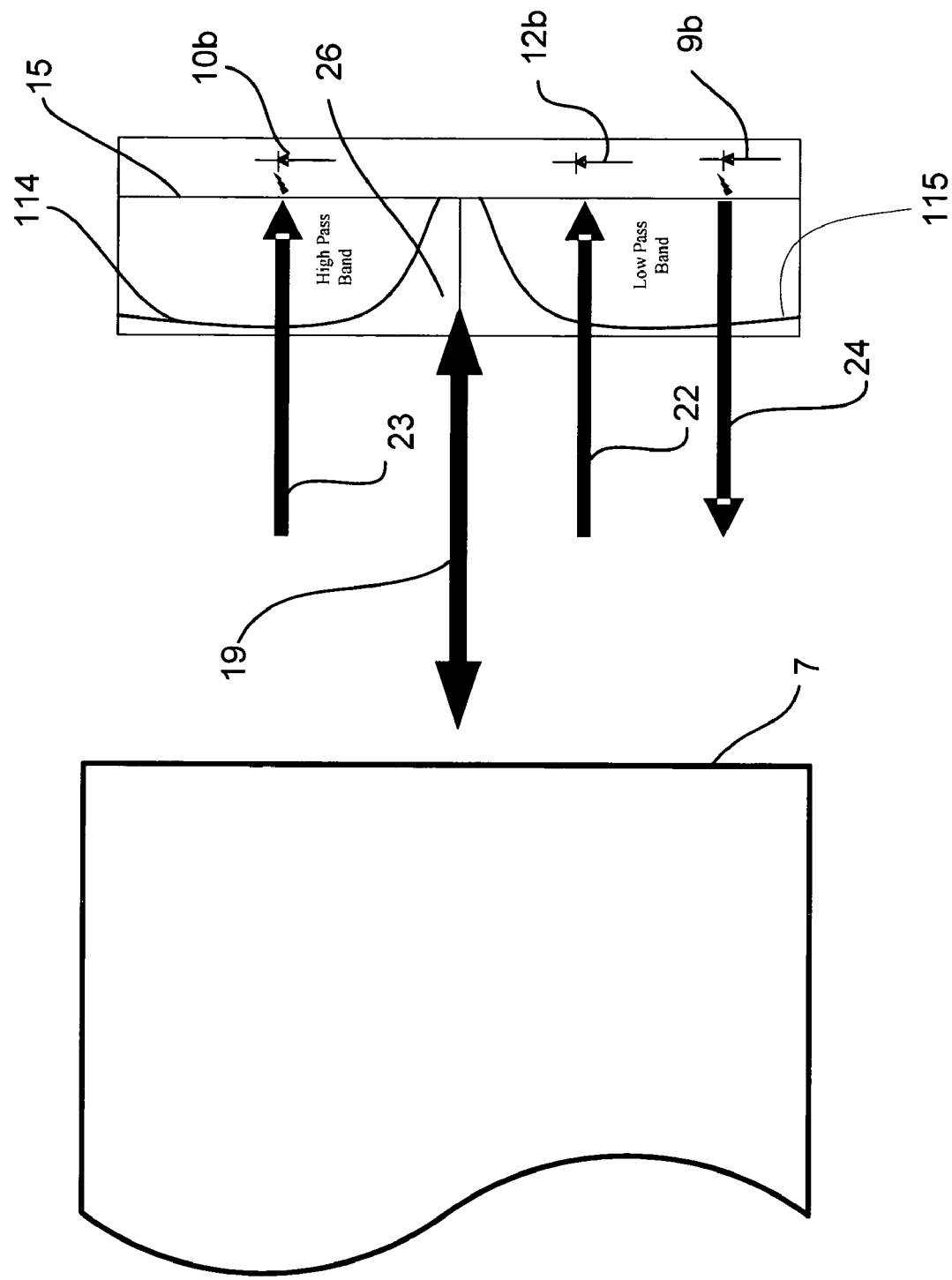
FIG. 3 depicts simplified response characteristics of an optical filter in an end equipment unit.

Triplexer 15 also acts as a filter. It allows different photodetectors to receive only signals in the passband intended for them, and strongly attenuates signals in other bands. A simplified filtering characteristics of the triplexer 15 is depicted in FIG. 3. As can be seen, the triplexer accepts a high pass band 114 and a low pass band 115, with a distinct rejection zone 26 therebetween. Signals in the rejection zone are the signals that will be maximally attenuated from any of the signal sources like 12b and to photodetectors 9b and 10b, within the bands in which the equipment is designed to operate.

As the photodetectors and other equipment can only handle a given amount of power before it is damaged, the use of an OTDR frequency that lies in the rejection zone maximizes the protection provided to the sensitive components of the ONT. Therefore OTDR interface 20 is tuned to a frequency within the rejection zone of the ONT triplexer. This provides two distinct advantages: Firstly, as the OTDR signal is out of band, it allows testing of the network without interfering with the network payload, so service to the user is not disrupted. Furthermore, the use of an OTDR frequency that will be most attenuated by the ONT triplexer allows use of higher power test pulses at the OTDR frequency as the OTDR signal will not reach sensitive components, or will reach them at greatly reduced power level.

Therefore, the OTDR in the present invention is tuned to a frequency that is selected to lie in the rejected zone.

The skilled in the art will recognize that the use of higher power test pulses offer significant testing and diagnosis advantages. In typical present applications attenuation of 60 dB or more between the OTDR pulse delivered to the network and the received reflection are common. The use of a reflection of higher power will allow better analysis of the reflected signal, avoid undetected signals, and thus increase the usability of the test.

Figure 4:
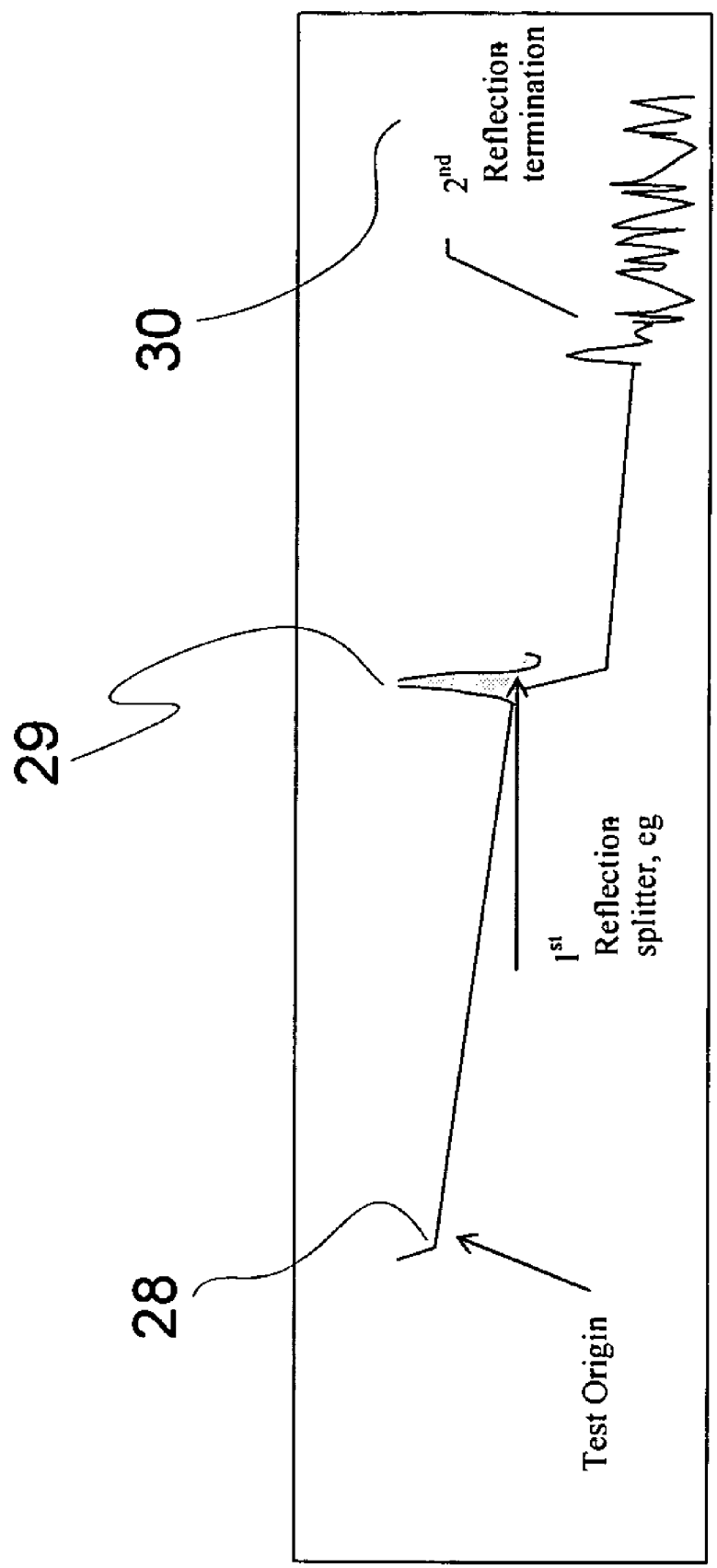
FIG. 4 depicts schematically temporal reflections from a network.

In an optional preferred embodiment of the invention, allows further analysis of the test signals. FIG. 4 depicts a schematic, simplified example of a 'signature' of a network (not to scale). The x axis depicts time, and the Y axis depicts signal strength. At 28 a test pulse is sent from the OTDR interface 20 to the combiner 2 and sent down the network. 29 shows a typical reflection returned from the splitter, while 30 depicts reflection returns from the end equipment, i.e. the ONT's at the end of feeder fibers 7. The signature is characteristic of the network actual configuration at the time of the test. Naturally, any impairments will observable in the returns.

In the preferred embodiment, the network is tested prior to placing it into service, and the signature as saved as a baseline signature. Thereafter, the network is tested periodically and a 'current' i.e. most recently obtained signature is generated. Differences between the baseline signature and the current signatures are analyzed. It should be noted that any signature taken prior to the 'current' i.e. most recent signature may be used as a baseline, and will equally serve to detect differences between the current and previous signature.

Figure 5:
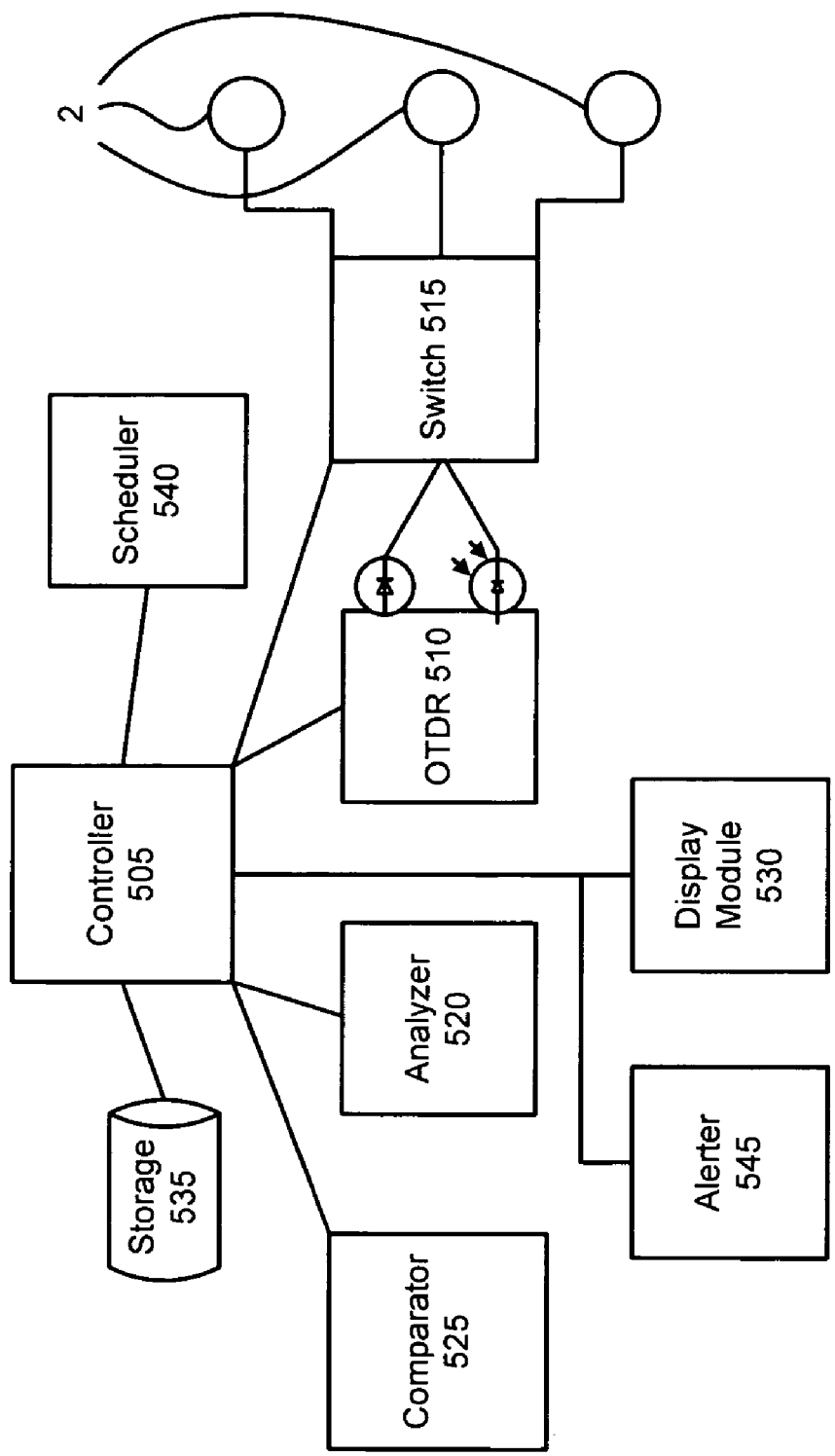
FIG. 5 depicts an apparatus in accordance with the preferred embodiment of the invention.

FIG. 5 Depicts a preferred embodiment of an Optical Test Node (OTN) 3 in greater detail in accordance with the preferred embodiment of the present invention. A central controller 505 controls the operation of the different portions of the OTN. The OTN further comprises an OTDR 510 that transmits signals to the network at a frequency which lies in the rejection zone, receives reflections, and measure characteristics of the reflected wave (in this embodiment the OTDR 510 comprises the OTDR interface 20, as well as the auxiliary circuits 35 of the OTDR). By way of example the characteristics may comprise time delay between the transmitted pulse and the reflection, amplitude of the reflection, the reflected wave envelope, and the like. In the preferred embodiment the OTDR is integrated within the OTN, but discrete implementation is equally contemplated.

In the preferred embodiment, a switch 515 is operable under the control of controller 505. The switch is used for testing more than a single trunk fiber with its associated feeders. The switch switches the signals between a plurality of combiners 2, each coupled to a trunk fiber. The switching arrangement depicted in the drawing is for illustration purpose and the skilled in the art of optical distribution networks will recognize other arrangement for switching and distributing the OTDR signal.

When the reflection of the OTDR test signal is received and measured by the OTDR, the results are preferably transferred to the optional analyzer 520. The analyzer may be a separate module such as a separate computer, or in the preferred embodiment it is a part of the OTN that operates under the control of controller 505, either as a program for operating controller 505, or as dedicated circuitry, or as a combination thereof. The analyzer analyzes the signal for a plurality of characteristics, for example deciding if the time between the transmitted pulse and the reflection is indicative of a problem, if all expected reflections have been received, if the strength of the reflected signal is sufficient, and the like. The analyzer further may be utilized to analyze the returned signal against an expected response masks such as responses received from other networks of similar configurations or more preferably from a model for predicting the network behavior and the nature of reflected signals therefrom.

Analyzer 520 is an optional device, and the OTDR signal may be transferred directly to comparator 525. In the preferred embodiment, comparator 525 is used to compare the OTDR data with other data. Most preferably, the OTDR data is compared to a baseline signature of that specific network or network segment. Therefore, by way of example, prior to a network segment such as a trunk fiber is being put into service, a baseline signature is being obtained and stored in storage 535. Then, either manually, or preferably under the control of scheduler 540, a new test is carried out, to produce a current signature. The results of the current signature are being analyzed with the base signature. More than one base signature may be stored, and the comparison may be made against any baseline signature that was taken prior to the current signature. In the most preferred embodiment, the current signature or portions thereof are used to update one or more baseline signatures, to accommodate for normal deterioration of the network. Clearly such signature may be obtained for several parts of the network such as trunk fibers, splitters, feeder fibers, OTN's, and the like.

A display module 530 is utilized to display different results such as the results of analysis, results of comparison, and optionally even raw data. An optional alerter 545 is used to alert users of test results that divert from guidelines to allow early response to network deterioration that exceeds preset limits.

Figure 6:
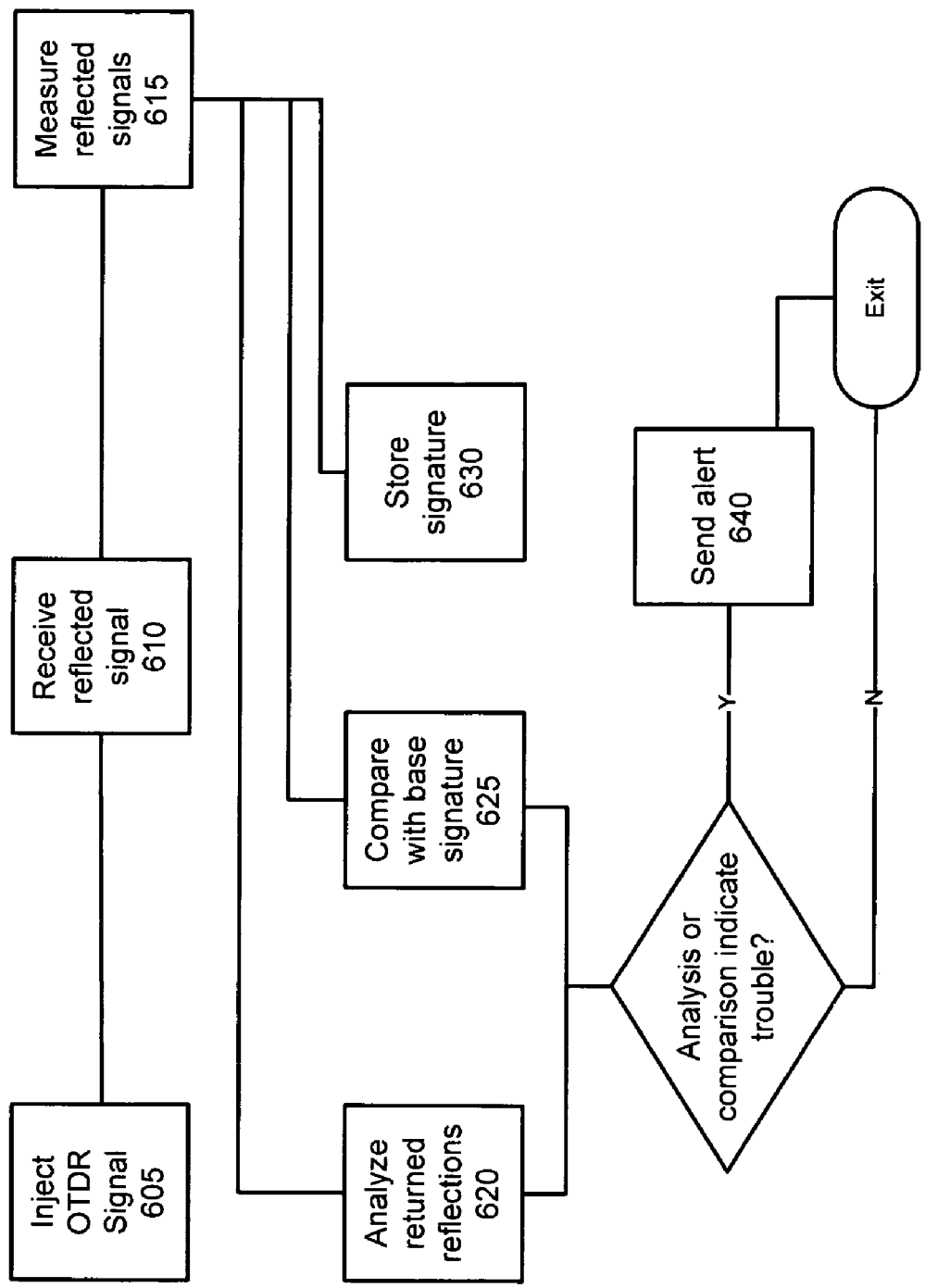
FIG. 6 represents a simplified flowchart showing operation of the preferred embodiment of the invention.

A flowchart of a method in accordance with another aspect of the present invention is depicted in FIG. 6. An OTDR signal having a frequency in the rejection zone of an optical filter installed in network end equipment is injected 605 into the trunk fiber. A reflected signal is received 610 and measured 615. Optionally, the returned reflections are analyzed 620. Further optionally the measured results are compared with a baseline signature 625. The measurement results may be stored 630, and/or utilized to modify a baseline signature, or may become a baseline signature itself. Further optionally, if the results of either the analysis step or the comparison step or both are outside preset boundaries, an alert is issued 640. Such alert may be visual, aural, or by any other convenient manner such as an e-mail, paging, cellular alert, wireless alert, telephone call, and the like.

Figure 7:
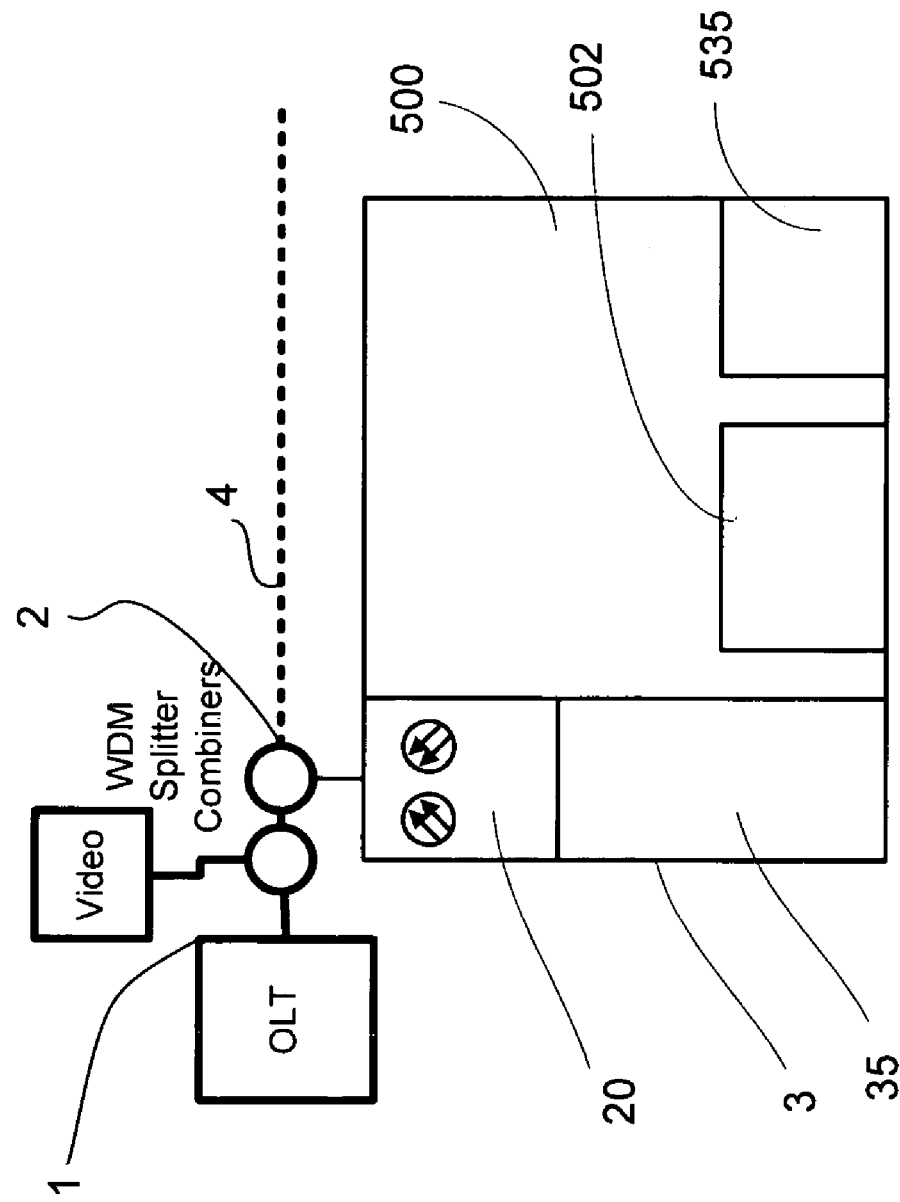
FIG. 7 represents yet another schematics embodiment of an Optical Test Node according to an optional embodiment.

To the skilled in the art it will be clear that while the network topologies described herein in detail are PON and FTTP, the invention clearly extends to other topologies. Also it will be clear that different modules such as the analyzer, alerter, comparator, and the like may be implemented both as a software that operates on a generator special purpose computer, as well as utilizing specialized circuitry. Similarly, modules that are described as integrated may be implemented separately such as the switch, the OTDR, or different portions of the OTN. All such modifications clearly fall within the scope of the invention. By way of example FIG. 7 depicts a preferred embodiment of the OTN 3, wherein a computer 500 having a computer program 502 and access to storage 535 is coupled to or integrated with, an OTDR which utilizes the optical front end 20 to interface with the optical network, together with auxiliary circuitry 35 which may comprise timing, trigger, power, and similar circuits.

The skilled in the art will further realize that the OTDR signal will often contain, either due to equipment limitations or due to design choice, other frequencies that may not lie within the frequency rejection zone. When such frequencies lie within the payload frequency bands they will have far lower energy levels than the OTDR frequency within the rejection zone. Thus the OTDR signal which lies within the rejection zone is considered the primary frequency. An OTDR with a primary frequency in the rejection zone range differs from a scanning OTDR, or devices producing substantially uniform multi-frequency signals, within the payload bands frequency as well as within the rejection zone frequencies.

which scans a band that extends beyond the rejection zone at substantially equal signal levels, It will be appreciated that the invention is not limited to what has been described hereinabove merely by way of example. While there have been described what are at present considered to be the preferred embodiments of this invention, it will be obvious to those skilled in the art that various other embodiments, changes, and modifications may be made therein without departing from the spirit or scope of this invention and that it is, therefore, aimed to cover all such changes and modifications as fall within the true spirit and scope of the invention, for which letters patent is applied.

What is claimed is:

1. A system for testing optical networks in an optical network having a trunk optical fiber having a proximal and a distal ends, the trunk being coupled to at least one splitter at its distal end, the splitter being further coupled to a plurality of feeder optical fibers, at least one of the feeder fibers being coupled to an Optical Network Terminal (ONT), the ONT having an optical passband filter having a at least one optical frequency rejection zone for attenuating signals in frequencies within the rejection zone, the system comprising:

an Optical Time Domain Reflectometer (OTDR) coupled to the trunk at or near its proximal end;

wherein the OTDR having a transmitter tuned to produce optical waves in a primary frequency within the rejection zone, for the OTDR to couple transmitted waves to the trunk; and a receiver tuned to receive reflected optical waves at a primary frequency within the rejection zone, for receiving the transmitted optical waves reflected from the optical network, wherein a set of reflected waves forms a first signature; and, wherein the optical filter is characterized with at least one high passband and at least one low passband, and wherein the rejection zone is interposed between the high passband and low passband.

2. A system as claimed in claim 1, further constructed to analyze the signature.

3. A system as claimed in claim 2, wherein the analysis comprises comparison of the first signature with a second signature.

4. A system as claimed in claim 3 wherein the second signature is a calculated model of an expected signature, or a signature previously obtained from the network.

5. A system as claimed in claim 3, wherein the system is constructed to produce an indication if the results of the comparison diverge from a predefined parameter.

6. A system as claimed in claim 1, further constructed to analyze the first signature and to produce indication of problems in the network if the first signature diverges from a predefined parameter.

7. A system as claimed in claim 6, wherein the indication is selected from a group consisting of visual indication, telephonic indication, audible indication, paging indication, cellular indication, voice message indication, light indication, or a combination thereof.

8. A system as claimed in claim 1, further comprising a computer coupled to the OTDR, and wherein the OTDR is constructed to provide the computer with data relating to the amplitude of the reflected optical wave, or to the attenuation level of the reflected wave.

9. A system as claimed in claim 1 wherein the splitter is an active optical splitter.

10. A system as claimed in claim 1, wherein the optical network is an ITU G.983 standard conformant network.

11. A method for in service testing optical networks, in an optical network having a trunk optical fiber having a proximal and a distal ends, the trunk being coupled to a splitter at its distal end, the splitter being further coupled to a plurality of feeder optical fibers, at least one of the feeder fibers coupled to an Optical Network Terminal (ONT), the ONT having an optical passband filter having at least one optical frequency rejection zone for attenuating signals in frequencies of the optical filter rejection zone, the method comprises the steps of:

coupling optical waves having a primary frequency within the rejection area to the proximal end of the trunk fiber;

receiving reflected optical waves from the optical network; and measuring characteristics of the reflected waves to obtain a first signature;

wherein the reflected waves are reflections of the optical waves coupled in the step of coupling; and wherein the optical filter is characterized with a high passband and a low passband, and wherein the rejection zone is interposed between the high and low passband.

12. A method as claimed in claim 11, further comprising the step of analyzing the first signature.

13. A method as claimed in claim 11, further comprising the step of storing the first signature of the tested network.

14. A method as claimed in claim 11, further comprising the step of comparing the first signature with a second signature.

15. A method as claimed in claim 14, wherein the second signature is a calculated model of an expected signature, or a signature previously obtained from the network.

16. A method as claimed in claim 14, further comprising the step of producing an indication if the results of the comparison diverge from a predefined parameter.

17. A method as claimed in claim 16, wherein the indication is selected from a group consisting of visual indication, telephonic indication, audible indication, paging indication, cellular indication, voice message indication, light indication, or a combination thereof.

18. A method as claimed in claim 11, wherein the optical network is an ITU G.983 standard conformant network.

* * * * *